United States Patent [19]
Cook et al.

[11] Patent Number: 5,738,992
[45] Date of Patent: *Apr. 14, 1998

[54] MULTIPLE OUTPUT REFERENCING SYSTEM FOR EVANESCENT WAVE SENSOR

[75] Inventors: Thomas A. Cook, Corning, N.Y.; Rudolf E. Slovacek, Norfolk, Mass.; Walter F. Love, Horseheads, N.Y.; Richard L. Schulkind, Sharon; Irene M. Walczak, Boston, both of Mass.

[73] Assignee: Chiron Corporation, E. Walpole, Mass.

[*] Notice: The term of this patent shall not extend beyond the expiration date of Pat. No. 5,340,715.

[21] Appl. No.: 629,595

[22] Filed: Apr. 9, 1996

Related U.S. Application Data

[62] Division of Ser. No. 246,391, May 20, 1994, Pat. No. 5,525,466, which is a continuation of Ser. No. 712,304, Jun. 7, 1991, abandoned.

[51] Int. Cl.$^6$ ..................... G01N 33/552; G01N 33/543
[52] U.S. Cl. ............... 435/6; 385/12; 385/129; 385/130; 385/141; 356/243; 356/306; 356/448; 422/82.05; 422/82.08; 422/82.11; 435/287.1; 435/287.2; 435/288.7; 435/808; 436/164; 436/172; 436/518; 436/527; 436/805
[58] Field of Search ............... 385/12, 141, 142, 385/143, 129, 130; 356/243, 306, 448; 422/82.05, 82.08, 82.11; 435/6, 287.1, 287.2, 288.7, 808; 436/164, 172, 518, 527, 805

[56] References Cited

U.S. PATENT DOCUMENTS

| | | | |
|---|---|---|---|
| 3,998,591 | 12/1976 | Edfeldt | 23/253 R |
| 4,199,559 | 4/1980 | Ullman et al. | 424/8 |
| 4,261,968 | 4/1981 | Ullman et al. | 424/8 |
| 4,447,546 | 5/1984 | Hirschfeld | 436/527 |
| 4,558,014 | 12/1985 | Hirschfeld et al. | 436/527 |
| 4,582,809 | 4/1986 | Block et al. | 436/527 |
| 4,608,344 | 8/1986 | Carter et al. | 436/34 |
| 4,654,532 | 3/1987 | Hirschfeld | 250/458.1 |
| 4,671,938 | 6/1987 | Cook | 422/57 |
| 4,775,637 | 10/1988 | Sutherland et al. | 436/527 |
| 4,810,658 | 3/1989 | Shanks et al. | 436/172 |
| 4,822,746 | 4/1989 | Walt | 436/528 |
| 4,852,967 | 8/1989 | Cook et al. | 350/96.29 |
| 4,880,752 | 11/1989 | Keck et al. | 435/7 |
| 5,156,976 | 10/1992 | Slovacek et al. | 436/164 |
| 5,340,715 | 8/1994 | Slovacek et al. | 435/6 |
| 5,525,466 | 6/1996 | Slovacek et al. | 435/6 |

FOREIGN PATENT DOCUMENTS

| | | |
|---|---|---|
| 0 184 600 | 6/1986 | European Pat. Off. |
| 0 185 126 | 6/1986 | European Pat. Off. |
| 0 209 489 | 1/1987 | European Pat. Off. |
| WO 89/09408 | 10/1989 | WIPO |

OTHER PUBLICATIONS

Stewart, G. et al. Referencing Systems for Evanescent Wave Sensors, *Proc. Of SPIE* 1314, 262 (1990).

Bluestein, B.I. et al. Fiber Optic Evanescent Wave Immunosensors for Medical Diagnostics *Biotech.* 8, 16 (1990).

Sutherland, R.M. et al. Immunosensors at a Quartz Liquid Interface, Theory *J. Immuno. Methods* 74, 25 (1983).

*Primary Examiner*—Christopher L. Chin
*Attorney, Agent, or Firm*—Arthur S. Morgenstern; Stanley Sacks; Robert P. Blackburn

[57] ABSTRACT

An evanescent wave system and method including an optical sensor for use in assaying a reference material and at least one molecular species or analyte in a test medium or test sample for diagnostic and other applicable purposes. The sensor includes a waveguide for propagating a radiation input along its length. The radiation input causes evanescent electromagnetic waves that are capable of stimulating output emissions that are indicative of a reference material and of one or more molecular species or analytes. By comparing the emission(s) indicative of the reference material to the emission indicative of the presence of the molecular species or analyte, the presence and concentration of the molecule in the sample can be determined. The reference material provides for normalization and/or calibration of the system.

26 Claims, 9 Drawing Sheets

MULTIPLE OUTPUT REFERENCING SYSTEM FOR EVANESCENT WAVE SENSOR

CROSS-REFERENCE TO RELATED APPLICATIONS

The present application is a divisional application of U.S. patent application Ser. No. 08/246,391 filed May 20, 1994, now U.S. Pat. No. 5,525,466 which is a continuation application of U.S. patent application Ser. No. 07/712,304, filed Jun. 7, 1991, now abandoned.

FIELD OF THE INVENTION

This invention relates to an evanescent wave system; including an optical processor, sensor, for use in assays of one or more analytes or molecules in a test medium, and a reference material, and more particularly, to such a sensor which generates two or more output signals from one or more wave propagating surface. The reference material provides for normalization and/or calibration of the system.

TECHNICAL DISCLOSURE

There are a number of optical devices which propagate radiation by "total internal reflection", see Harrick, N. J., *Internal Reflection Spectroscopy*, Harrick Scientific Corp., Ossining, N.Y. (Third printing 1987), to generate an evanescent wave at the interface of the device and a medium or test sample having a lower index of refraction. The evanescent wave is an electromagnetic waveform which typically extends less than a wavelength into the test medium. However, this penetration is sufficient to permit interaction between the evanescent wave component and an analyte in the medium.

One example of such devices is the use of waveguides in the area of fluorescent immunoassays. Waveguides in the form of fiber optic waveguides are coated with a reactant coating including for example either an antibody or an antigen, which binds the corresponding antigen or antibody, respectively, if present, in a medium. This reactant coating is typically attached to the waveguide prior to the performance of the assay. In a "sandwich" immunoassay, an antibody is coated to the surface of the fiber optic waveguide to form a reactant coating, and the waveguide is contacted with a medium believed to contain the antigen (analyte) to be analyzed, and an added second antibody, previously labelled with a fluorescent molecule. Alternatively, in a "competitive" assay, a fluorescently labelled antigen is first mixed with the medium suspected of containing an antigen and the mixture is brought into contact with the reactant coated waveguide. In either technique, the coated antibody binds with the antigen to form a complex attached to the fiber optic waveguide.

Electromagnetic radiation is introduced into the fiber optic waveguide at one or more predetermined sets of wavelength bands and is propagated along the waveguide by "total internal reflection". The reflection is, of course, not completely total as, for example, a fluorescent molecule absorbs a small amount of evanescent radiation.

The attached fluorescent molecule (referred to as a fluorophore) absorbs energy from the evanescent wave at a first set of wavelengths and fluoresces at a second, longer set of wavelengths. Fluorescence from the excited fluorophore passes into the optical waveguide via a tunneling effect and the portion of the fluorescent radiation which passes within the waveguide at an angle greater than the critical angle is propagated through the waveguide to emerge as an output signal.

Several improved waveguides are described by Keck et al. in U.S. Pat. No. 4,880,752; which is incorporated herein by reference. In one construction, the waveguide has an elongated, rod-shaped core having an opening within the core material. A reactant coating is disposed about the opening within the core on a single optical surface.

There is, however, a need for providing an evanescent sensor which can normalize or calibrate-for variations in signal input and signal collecting efficiencies as well as defects in the optical surface or geometry. For example, a decrease in diameter along the length of a solid rod or of wall thickness of a hollow fiber optic waveguide changes the angle of light input at which light is totally internally reflected. This may cause the radiation to eventually strike the waveguide surface less than the critical angle and therefore escape the waveguide, changing the evanescent signal. Alternatively, if the diameter increases along the length of a rod or wall of the waveguide, the angle of light propagating therethrough may become increasingly greater than the critical angle, and there will be fewer reflections and a lower propagation angle, both of which reduce the of evanescent wave electromagnetic field strength which is delivered to a medium.

Another problem concerns irregularities in the wave propagating surface of the sensor, altering the amount of signal output detected.

OBJECTS OF THE INVENTION

Accordingly, it is among the objects of the invention to provide an improved evanescent wave system where the system's apparatus includes a sensor, for use in assays of analytes or molecules in a medium or test sample and a reference material, and more particularly, to such a sensor which generates two or more output signals from one or more wave propagating surfaces. The reference material provides for normalization and/or calibration of the system.

A primary object of the invention is to provide an optical processor for a multifrequency evanescent wave system.

Another object of the invention is to provide an evanescent wave sensor having two or more fluorophores.

Yet another object of the invention is to provide an evanescent wave system including a sensor and a reference material, the reference material functioning to normalize and/or calibrate for variations in the sensor and instrument to sensor coupling efficiency which affect the signal input and signal collection.

A still further object of the invention is to provide sensor that allows at least one analyte and a reference material to be analyzed by a wave propagating surface.

Another object of the invention is to provide an evanescent wave system which can compensate for variations between different sensors.

Yet another object of the invention is to provide an evanescent wave system including a sensor that provides accurate output signals that are corrected for changes in those things which cause signal variations by the sensor.

Another object of the invention is to provide a sensor incorporating a reference material.

SUMMARY OF THE INVENTION

In a first embodiment of the invention, analysis of both one or more analytes and a reference material is achieved by attaching a reactant coating and a reference material onto an evanescent sensor, and in a preferred embodiment on the same wave propagating surface from which the reference material and analyte(s) are sensed in the evanescent zone. The reference material functions to normalize and/or calibrate the system. Alternatively, the reference material may be physically independent of the sensor and yet still function to normalize and/or calibrate the system.

In use, the invention allows output signals from both the reference material and the analyte to be detected so as to provide a means for normalizing and calibrating the system for any variations in the sensor and instrument to sensor coupling efficiency which affect the signal input and signal collection. See Harrick, infra, and Love, W. F., Bulton, L. J., and Slovacek, R. E., "Optical Characteristics of Fiber Optic Evanescent Wave Sensors" printed in *Biosensors With Fiberoptics*, D. Wise and L. Wingard, Editors, Humana Press, Clifton, N. J.; both of which are incorporated herein by reference. Since any geometric variations or surface irregularities in the sensor will affect the known output signal from the reference material in the same manner as the signal from the analyte, a ratio of the output of the analyte signal to the output of the reference signal provides a value that will vary only with differences in the analyte and not with differences between sensors. To avoid difficulty in the analysis of the output signals, the reference material must be selected to provide an output signal wavelength that is different and/or readily distinguishable from the signal that is indicative or representative of the analyte. The reference material is used for signal normalization and/or calibration of the system in order to provide accurate and precise test results; and may be measured prior to, during or after the analyte measured signal.

Further advantages and objectives of the reference material include testing the effects of aging on the reactant coating; correlation of substrate and coating variability between sensors in a given manufacturing batch, lot, or assay; and examining variations due to sensor manufacture or handling during coating. The use of the reference material further provides the advantages of detecting defective sensors i.e. a waveguide having a wave propagating surface irregularity, including for example a scratch or chip.

In a second embodiment of the invention, multiple analytes can be sensed or detected using a single sensor. One or more wave propagating surfaces may be utilized for various assay formats. In one example of this embodiment, the test sample to be analyzed will contain one or more antibodies for analyte antigens, in which each one or more of the antibodies are labelled with fluorophores that emit different output wavelengths or signals on exposure to the evanescent wave. If determination of only the relative amount of the individual analyte is desired, this value can be directly determined by comparing the individual output signals. Alternatively, if an absolute analyte value is desired, a reference material, as described above, can in one embodiment of the invention be incorporated onto the same wave propagating surface from which the analyte is sensed. The reference material must be selected to provide an output signal wavelength that is either the same or different than that of the analyte.

In a third embodiment of the invention, an assay can be performed in which the two analyte fluorophores overlap in their wavelength absorption and emission bands; provided that proper fluorescent molecules are selected for the individual analytes.

In a fourth embodiment of the invention the reference material is added to the test medium believed to contain the analyte to be detected, and the evanescent reaction carried out as described above.

In a fifth embodiment of the invention, the reference material is used as a reference material for itself. In an example of this embodiment, a fluorophore reference material is used as a reference for itself. This embodiment provides the advantage of a reduced signal to noise ratio vs. a two fluoromer system.

Each embodiment of the invention is operable in a system including an optical processor.

DESCRIPTION OF THE DRAWINGS

The foregoing and other objects and advantages of the invention will be appreciated more fully from the following further description thereof with reference to the accompanying drawings wherein.

DETAILED DESCRIPTION OF THE INVENTION

An evanescent wave system is described including a sensor, reference material and an operation means, and a method for using the system. An optical processor is a component of the system. In one embodiment, the sensor comprises two planar parallel surfaces, whereas in a preferred embodiment, the sensor comprises a waveguide having a wave propagating surface, as in the case of a strand or cable.

The sensor receives a radiation input and emits one or more output signals indicative of the presence of one or more analytes and a reference material in the evanescent wave region (Harrick, infra and Love et al infra). In the case of a waveguide, the wave propagating surface is capable of receiving a radiation to excite a reference material, the same radiation, if desired, also exciting at least one analyte or a receiving a sequential or simultaneous excite at least one analyte complex. The sequence of introducing radiation to excite the reference material or analyte may be varied as necessary in the practice of various test methods.

In the case of the sensor having two separate parallel, planar surfaces, the input light is propagated between the two surfaces. A single surface is capable of receiving at least a first radiation input and generating a signal output indicative of the presence of a reference material as well as a radiation output signal indicative of the presence of at least one analyte.

One characteristic of the invention is that the evanescent wave electromagnetic fields generated at the wave propagating surface interact with one or more analytes at the interface between the waveguide and a test medium. Test mediums may include a gas, liquid or solid. In one configuration, for example, the wave propagating surface is coated with a reactant coating complementary or specific to at least one analyte and coated with a reference material that absorbs light in a set of wavelength bands and emits light at a different set of wavelength bands. The reference material includes fluorophores, chemiluminescent materials, time resolved fluorophores and luminescent compounds. In one example, the reactant coating of the wave propagating surface binds at least one analyte which in turn binds a homologous binding partner carrying a fluorescent molecule. The binding partner and the reference material may be attached to the surface simultaneously or sequentially by covalent or noncovalent means. In another configuration only an analyte binding partner is attached to the surface; with the reference material being added to the test medium. A fluorophore reference material and the fluorescent labelled molecule can be selected so that both are excited by a set of wavelength bands and yet each emit an output signal at a different wavelength. Appropriate filters, if necessary, for signal input and signal output would be utilized in the apparatus to practice the invention as described below. The two different emitted fluorescent radiation wavelength(s) reenter the waveguide and are detected to enable accurate determination of the presence or quantity of one or more analytes. These configurations and a number of alternative configurations are described in more detail below or will become apparent to those skilled in the arts.

As stated above, there are a number of different configurations of an evanescent wave sensor to provide one or more wave propagating surfaces. One configuration involves a planar plate such as a microscope slide. Alternatively, a second configuration involves a hollow waveguide; while the third may be one as described in Slovacek et al, U.S. Pat. No. 5,156,976 entitled "Evanescent Wave Sensor Shell and Apparatus" and; a fourth and preferred construction is that of a solid cylinder such as a waveguide, and more particularly an optical fiber.

There are several factors to be considered in selecting a composition material for the sensor. One factor is that the material must have an index of refraction greater than that of the intended medium to be analyzed. Additionally, it is desirable for the material to be optically pure and provide low attenuation of the radiation of interest. Silica glass is suitable for ultraviolet or visible radiation, plastics such as polymethylmethacrylate (PMMA), polystyrene, and polycarbonate are suitable for visible radiation, and fluoride glass or chalcogenide are suitable for near infrared radiation. Other organic polymeric materials such as silicones, acrylates, fluoroacrylates, and the like can also be used as the sensor composition material. It is also desirable for the material to have negligible inherent fluorescence at the radiation wavelengths of interest for assays involving fluorescence. Other polymers and glass compositions would become apparent to those skilled in the art for application to various embodiments of this invention.

Additionally, it is desirable for the composition material to have suitable surface properties for attachment of reactant coating(s), including binding partners and reference materials, to it or to be made suitable or amendable to modification to assist attachment PMMA is the preferred embodiment material not only for its optical purity and its injection molding characteristics, but also because it is hydrophobic which enables antibodies and other molecules to be attached or absorbed to the surface simply by bringing them in contact with the PMMA. For glass, it is desirable to provide either a hydrophobic surface or one amendable to covalent and nocovalent coupling chemistries. A reactant coating as used herein shall be understood to include the attachment by coating means of a molecule which is receptive to a complementary molecule in a test medium to form a binding pair. Binding pairs include antibody-antigen, biotin-avidin and such other known substances which have a homologous substance as are known in the art. Coating as used herein shall be understood to include specific and nonspecific reactions including noncovalent binding and covalent binding.

Figure 1:
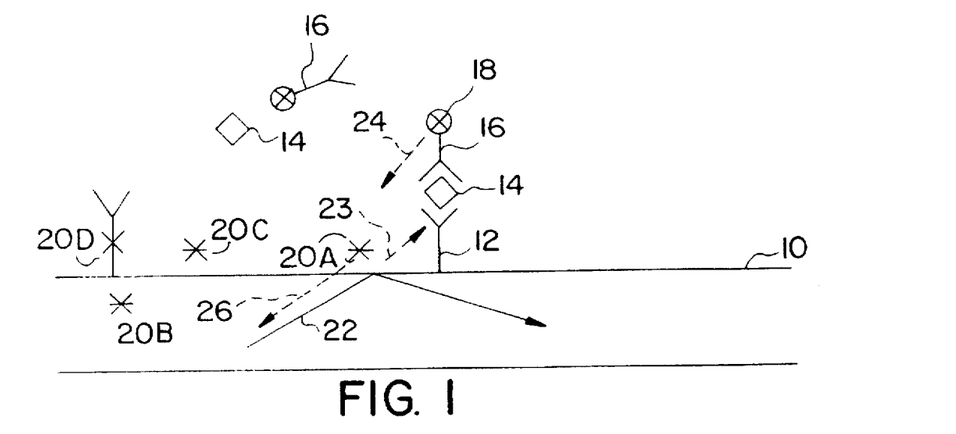
FIG. 1 is a schematic view of a portion of an evanescent wave sensor having a single analyte binding partner coated thereon and showing various formats of interactions of the reference material at the evanescent zone.

Referring to FIG. 1, an example of the present invention, in which a first fluorophore is attached to a surface 10 and a second fluorophore becomes attached to the surface is shown. A first bound antibody 12 binds analyte antigen 14 which in turn binds labelled antibody 16. The labelled antibody 16 is labelled by means of a fluorophore 18. In one example, the fluorophore 18 is B-phycoerythrin (BPE). A fluorophore reference material 20A, such as fluorescein, is attached to the surface 10. Analyte, as used herein, shall be understood to include any of a variety of chemical and biochemical substances. The use of the term analyte herein shall be understood to include both its singular tense and plural tense as appropriate. The analyte sources may include physiological, scientific and industrial (toxic and nontoxic) test mediums; where the presence, absence or quantity of the analyte in the medium is sought; and where, for example, analysis of a physiological analyte is relevant to diagnosis and treatment of a disease. Antibody as used herein shall be understood to include Fab antigen binding fragmentsm, univalent fragments Fab' and bivalent fragments F(ab')2.

Alternatively, the fluorophore reference material may be incorporated between two surfaces by reference 20B; or within the evanescent zone as shown by reference 20C; or as a component or label of the reactant coating as shown by reference 20D.

An excitation radiation input 22 is selected to excite emission within the evanescent wave zone from both the fluorophore reference material 20A-D and the fluorophore 18 on labelled antibody 16. When fluorophores 18 are BPE and fluorophore reference materials 20A-D are fluorescein, a radiation input 22 of light having an excitation wavelength of 480 nm excites, via an evanescent wave 23, a first emission signal 24 from the BPE antibody label at a wavelength of approximately 576 nm and a reference material emission signal 26 from the fluorescein reference material at a wavelength of approximately 520 nm to determine analyte and reference material, respectively. This example would utilize appropriate filters for signal input and signal output.

By comparing the relative signal of the analyte emission signal 24 to that of the reference material emission signal 26, substrate variations and signal variations are normalized and/or calibrated.

Figure 2:
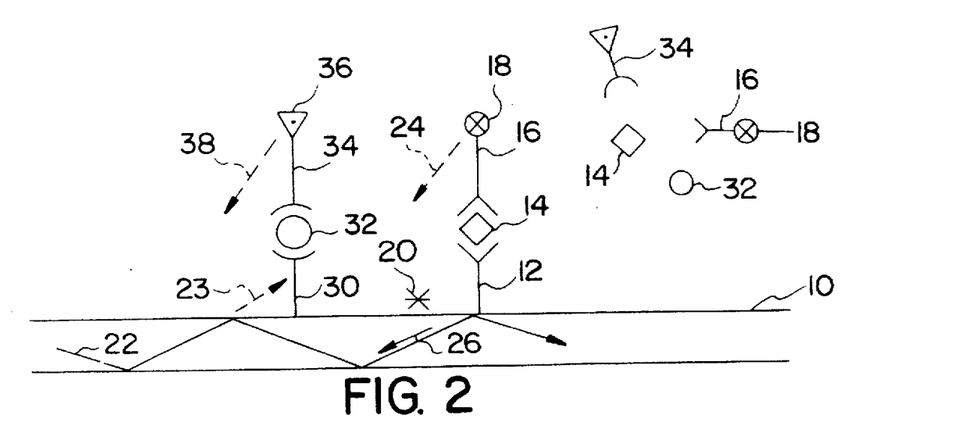
FIG. 2 is a schematic view of a portion of an evanescent wave sensor having a reference material and two analyte binding partners coated thereto.

Referring now to FIG. 2, a second embodiment of the present invention is shown in which a fluorophore reference material 20 is attached to the waveguide surface 10 and two separate fluorophore-labelled antibodies are in solution. A first attached antibody 12, binds with a first antigen 14 which, in turn, binds, labelled antibody 16. As in the previous example, the labelled antibody 16 is labelled with a fluorophore 18 such as BPE. Fluorophore reference material 20 such as fluorescein, is attached to the surface 10. Unlike the embodiment shown in FIG. 1, the embodiment shown in FIG. 2 includes a second attached antibody 30 as well as a corresponding second antigen 32 and second labelled antibody 34 both in solution. The second labelled antibody 34 is labelled with a second fluorophore 36 such as, for example, tris (2,2'-bipyridiyl) ruthenium II dichloride (referred to as ruthenium fluorophore herein).

As before, an excitation radiation input 22, is selected to be of a set wavelength band(s) that will provide an evanescent wave 23 to excite detectable emissions from the fluorophore reference material 20 and the fluorophores 18 and 36 on the respective labelled antibodies 16 and 34. In this example where the fluorophores 18 and 36 BPE and ruthenium, and fluorophore reference material 20 is fluorescein, a radiation input 22 of light having an excitation wavelength of 480 nm stimulates the first emission signal 24 from the BPE antibody label at a wavelength of approximately 576 nm, a second emission signal 38 from the ruthenium antibody label at a wavelength of approximately 610 nm and a reference material emission signal 26 from the fluorescein reference material at a wavelength of approximately 520 nm. This example would utilize appropriate filters for signal input and signal output.

Figure 3:
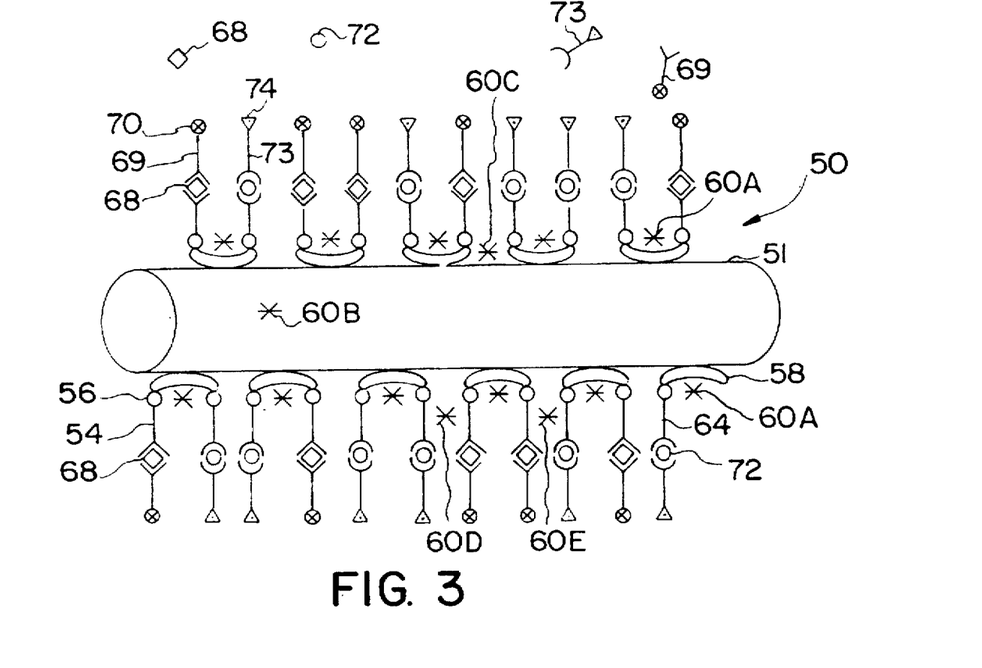
FIG. 3 is a schematic view of a portion of a cylindrical evanescent wave sensor having a reference material and two analyte binding partners bound to the surface via avidin.

FIG. 3 depicts a variation of the above example, in which the waveguide comprises a solid cylinder such as an optical fiber. Cylindrical waveguide 50 provides a means for assay of two or more analytes in a test medium and includes a reference material for normalization and/or calibration. Additionally, the waveguide surface is coated with avidin 58 to provide an initial coating surface. A first reactant coating includes a first antibody 54 which is biotinylated, (a biotin molecule 56 is attached to the antibody 54 to enable binding with the avidin 58). A second coating include second antibody 64 which is biotinylated to bind with the avidin 58. The surface also contains a biotinylated reference material dye 60A bound to the avidin coating, such as fluorescein.

Alternatively, reference material 60B can be a component of the said cylinder as shown in FIG. 3; or attached directly or indirectly to the surface as reference material 60C; bound to first antibody 54 as reference material 60D; bound to the second antibody 64 as shown by reference 60E; or depending on the type and format of the assay bound to the complementary or specific binding partner of the first or second antibody (not shown), or within the evanescent zone (not shown).

First antibody 54 binds with first analyte (antigen) 68 which in turn binds a first labelled antibody 69 which is labelled with a fluorescent molecule 70. Second antibody 64 binds a second analyte (antigen) 72 which in turn binds a second labelled antibody 73 carrying a fluorescent molecule 74 in a sandwich assay format. In one example, the first antibody 54 is anti-CKBB and the second antibody 64 is anti-CKMB; first fluorescent molecule 70 is TEXAS RED® fluorescent dye (trademark of Molecular Probes, Inc., Eugene, Oreg.) and second fluorescent molecule 74 is BPE.

Waveguide 50 is formed by coating outer surface 51 with avidin 58, or with strept-avidin, which is in solution at a concentration of approximately 200 micrograms per milliliter. Waveguide 50 is then coated with fluorophore reference material 60A in a dilute solution of biotinylated fluorescein and further coated with first antibody 54 in a solution containing biotinylated anti-CKBB at a concentration of approximately 50–200 micrograms per milliliter. In a preferred embodiment, a calculated amount of the fluorophore reference material 60A and first antibody 54 (biotin anti-CKBB) are coated on the waveguide.

When fluorescent molecule 70 is TEXAS RED® fluorescent dye and fluorophore reference material 60A is fluorescein, two peak emission wavelengths can be detected at 615 nm and 520 nm, respectively. In the analysis of two or more analytes, according to the present embodiment, a third output wavelength at 576 nm, for example, can be detected when a second fluorescent molecule 74 is BPE. Appropriate filters would be utilized for input and signal output.

Figure 4:
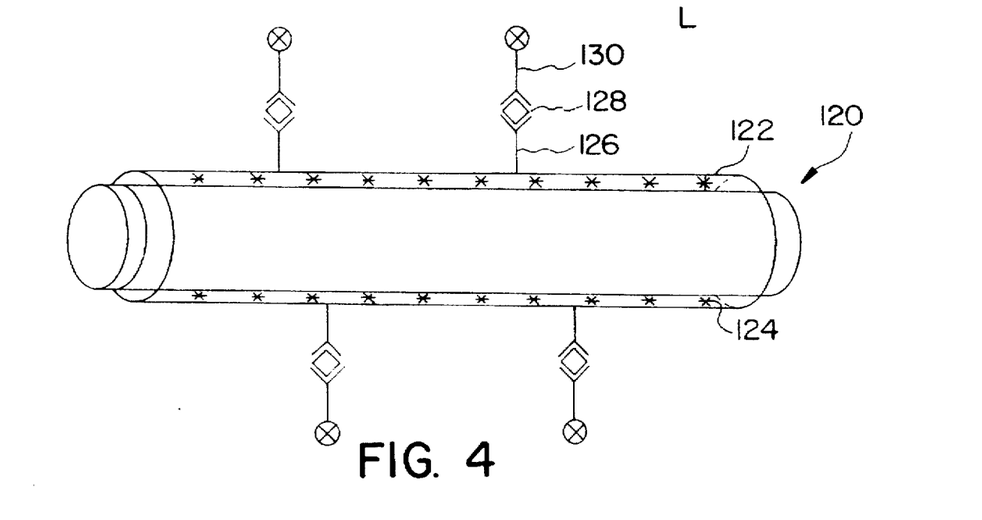
FIG. 4 is a schematic view of a portion of a cylindrical evanescent wave sensor having a reference material encapsulated in a coating on the sensor.

FIG. 4 shows a configuration in which the fluorophore reference material is encapsulated. This configuration is particularly desirable in circumstances in which it is necessary to physically isolate the fluorophore reference material from the test medium. A cylindrical sensor waveguide 120 has a surface coating 122 containing a fluorophore reference material 124. An antibody 126 for antigen 128 to be detected is attached to the surface. As noted above, if it is necessary to enhance binding Of the antibody 126 to the surface, binding partners, i.e. avidin-biotin and others known in the art, can be employed. Labelled antibodies 130 for antigen 128 are contained in test medium L along with the subject antigen 128. The labelled antibodies include fluorophores of the type described previously, as well as those which would be utilized by those skilled in the arts. The antigen 128 is allowed to bind with antibody 126 and also with labelled antibodies 130. Detection of the antigen is carried out in the manner previously described. Unlike the previous examples, however, the fluorophore reference material 124 is encapsulated within surface coating 122 on waveguide. Thus, undesirable interactions, i.e. charge-charge interactions, between the fluorophore reference material 124 and the antigen 128 and/or the labelled antibody 130 are reduced. Ideally, the refractive index of the encapsulating medium should be less than the waveguide refractive index so that the reference light is also generated according to evanescent wave principles. As before, multiple binding pairs can be employed allowing detection of multiple analytes.

Figure 5A:
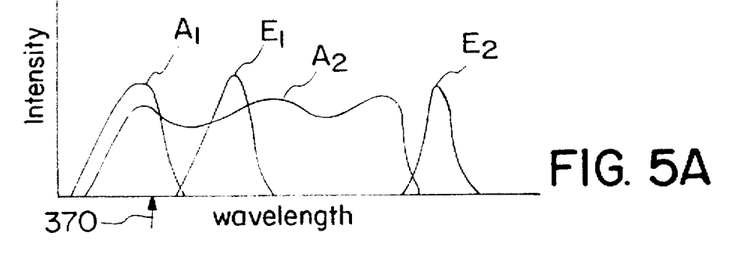
FIG. 5A is a graph of intensity versus wavelength showing overlapping absorption or excitation wavelengths and two different emission wavelengths.
Figure 5B:
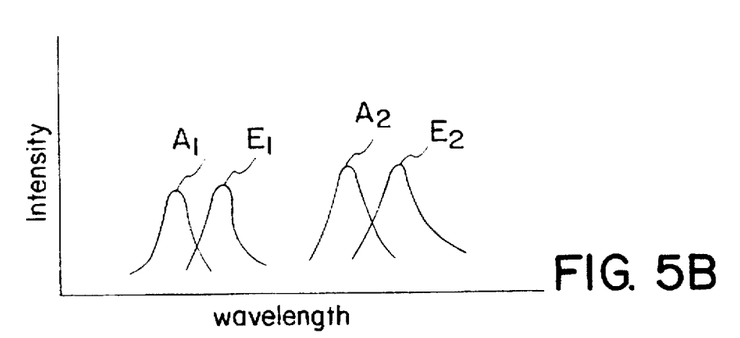
FIG. 5B is a graph of the spectra of two fluorophores having different absorption and emission wavelengths.
Figure 5C:
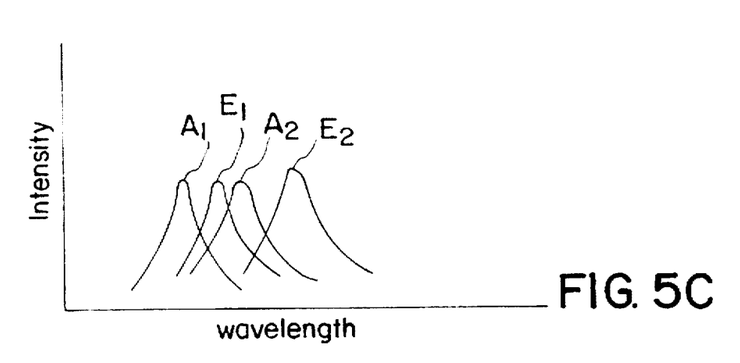
FIG. 5C is a graph of the overlapping spectra of the emission wavelength of a first fluorophore and the absorption wavelength of a second fluorophore.

Referring now to FIGS. 5A, 5B, and 5C, charts of different fluorophores having selected absorption and emission spectra are illustrated. These examples would utilize appropriate filters signal input and signal output.

FIG. 5A illustrates two fluorophores which have overlapping absorption spectra $A_1$ and $A_2$, such as for the dyes, fluorescein and RPE. Both fluorophores can therefore be stimulated by a single excitation set of wavelength bands, indicated by arrow 370 between 480–490 nm in this example. The fluorescein has an emission spectra $E_1$ which is different from emission spectra $E_2$ of RPE, and therefore two different output signals are generated.

FIG. 5B illustrates two fluorophores having different absorption and emission spectra. Neither the absorption spectra $A_1$ nor the emission spectra $E_1$ overlap with the second absorption spectra $A_2$ or the emission spectra $E_2$ of a second fluorophore. In one example, the first fluorophore is fluorescein and the second fluorophore is TEXAS RED® fluorescent dye.

FIG. 5 illustrates two fluorophores in which the emission spectra $E_1$ overlaps the absorption spectra $A_2$ of the second fluorophore is illustrated in FIG. 5C. One such set of dyes is fluorescein and BPE. Other combinations include BPE and Texas RED® fluorescent dye or C-phycocyanin and Texas RED® fluorescent dye.

Figure 6A:
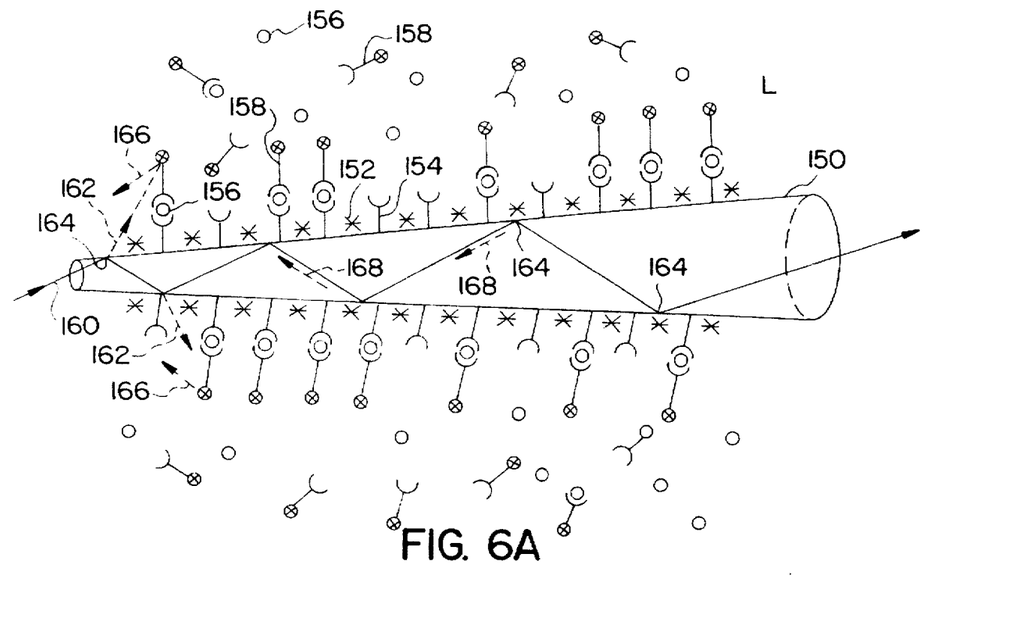
FIG. 6A is a schematic view of an evanescent wave sensor having a diameter that increases in the distal direction.
Figure 6B:
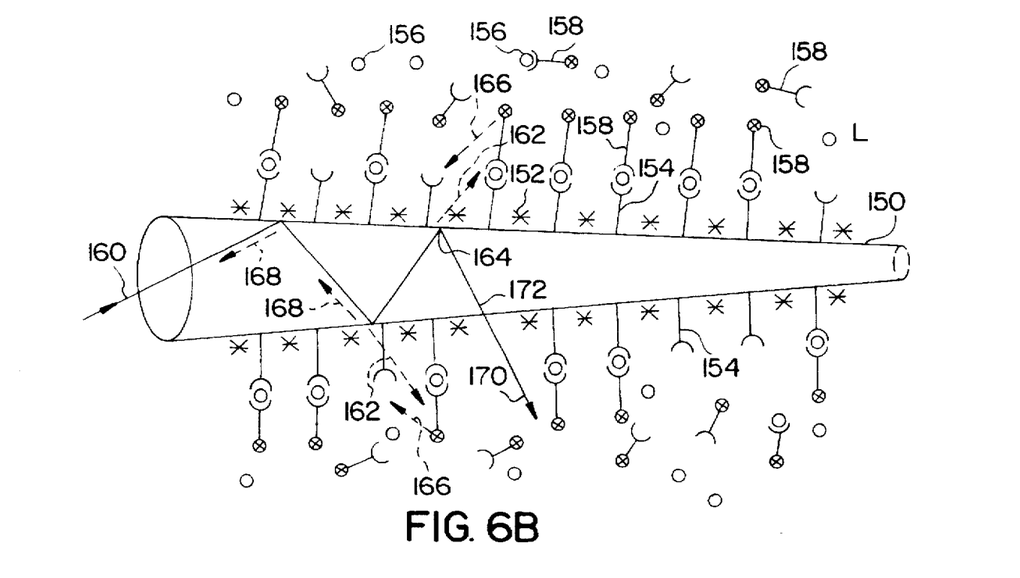
FIG. 6B is a schematic view of an evanescent wave sensor having a diameter that decreases in the distal direction.

Therefore, it can be seen that a number of dye combinations can be used with the embodiments of the present invention in the use of one or more wave propagating surfaces. In addition, one or more dyes may be used as reference materials. A partial listing of suitable dyes is presented in TABLE I. The use of alternate dyes and dye combinations to practice the invention as described herein will be apparent to those skilled in the art.

the radiation input wave. The sensor has a fluorophore reference material 152 and an antibody 154 attached thereto. Test medium L contains an antigen 156 to be analyzed and a labelled antibody 158 which can bind antigen 156 in a sandwich assay format. A light input 160 produces an evanescent wave 162 at each region of contact 164 with the wave propagating surface. Evanescent wave 162 stimulates an emission signal 166 from the labelled antibodies 158 which are bound to antigens 156 bound to antibody 159 on the waveguide. Evanescent wave 162 also stimulates emission of a reference signal 168 from fluorophore reference material 152 attached to the waveguide. Alternatively, fluorophore reference material 152 may interact with the waveguide as described above.

The signal output of the evanescent waves 162 varies partially in proportion to the number of bounces (reflections), or contacts 164, with the waveguide surface. However, for a waveguide of increasing diameter (as in FIG.

| Dye[1] | Abbreviation | Approximate ≥50% Absorption Wavelength Range (nm) | Excitation Wavelength (nm) | Emission Wavelength (nm) |
|---|---|---|---|---|
| Fluorescein isothiocyanate | FITC | 475–505 | 493 | 520 |
| Fluorescein | | 475–505 | 496 | 520 |
| R-Phycoerythrin | RPE | 480–570 | 495, 536, 566 | 576 |
| B-Phycoerythrin | BPE | 500–570 | 546 | 576 |
| Rhodamine B | | 500–585 | 578 | 604 |
| Texas Red® | TR | 580–610 | 596 | 615 |
| C-phycocyanin | CPC | 570–640 | 620 | 650 |
| Allophycocyanin | APC | 600–660 | 650 | 660 |
| R-phycocyanin | RPC | 545–635 | 555, 618 | 642 |
| Tris (2,2'-bipyridiyl) ruthenium II dichloride | RUTHENIUM | 410–490 | 450 | 610 |

[1]Source of dyes: Molecular Probes, Inc., Eugene, OR (USA)

The present invention describes a sensor utilizing a reference material which provides sensor normalization and/or calibration, to compensate for variations between different sensors or variations that result from fluctuations in the radiation input and signal collection. Variations between different sensors are generally of three types: a) geometric irregularities in which the optical surfaces are not maintained in a perfectly parallel relationship, b) surface irregularities resulting from damage to the waveguide surface, and c) light input variations due to the optical processor. Other variations between sensors include the age of the sensor and the use of the sensor. The reference material provides, when used for normalization and/or calibration, accurater test results, the ability to test the effects of aging of the reactant coating, substrate and coating variability correlation between sensors in a given manufacturing batch/lot or assay, the ability to examine variations due to sensor manufacture or handling during coating, and defective sensor detection. Further applications of the reference material will become apparent to those skilled in the arts.

FIGS. 6A and 6B illustrate the effect of signal variations caused by surface irregularities. Referring to FIG. 6A, a sensor 150 having an increasing diameter is shown. FIG. 6B shows a sensor 150 having a decreasing diameter. It is noted that the geometric variations depicted in FIGS. 6A and 6B are grossly exaggerated for purposes of illustration only. Additionally, as used herein, the terms increasing and decreasing diameter for the sensor are intended to refer to the diameter of the waveguide progressing in the direction of 6A), it is seen that the number of contacts 164 will decrease per unit length as the light input 160 travels along the waveguide. This decreasing number of contacts results in a lower evanescent wave signal output further along the waveguide, thereby decreasing the emission signal resulting from the presence of the analyte toward the distal end of the waveguide. However, since both the signal indicative of the presence of the analyte (antigen), and the reference signal 168 will be affected equally by the decreasing evanescent wave signal output, the ratio of the analyte emission signal 166 output to the reference material emission signal 168 output should remain constant for any given test medium. Thus, use of the fluorophore reference material 152 provides a means for compensating for variations among sensors in which the waveguide diameter increases.

Similarly, fluorophore reference material 152 provides a means to compensate for a waveguide having a decreasing diameter, as shown in FIG. 6B. The decreasing diameter causes the light input 160 to experience increasing reflection angles at the contact points 164, ultimately resulting in a signal loss once the critical angle for internal reflection of the signal 160 is passed. This signal loss is shown as light component 170 which exits the waveguide at region 172. Once light input 160 exits the waveguide, no evanescent waves are produced distal to exit point 172. Accordingly, no emission signal 166 indicative of the presence of analytes will be produced beyond the point at which light input 160 escapes the waveguide. As in the previous example, since both the analyte emission signal 166 and the reference material emission signal 168 will be affected equally by the loss of light input 160 beyond a certain point on the waveguide, the ratio of the emission signal 166 output to the reference material emission signal 168 output should remain constant for any given test sample. The use of the fluorophore reference material 152 provides a means for compensating for variations among sensors in which the waveguide diameter decreases.

Figure 7:
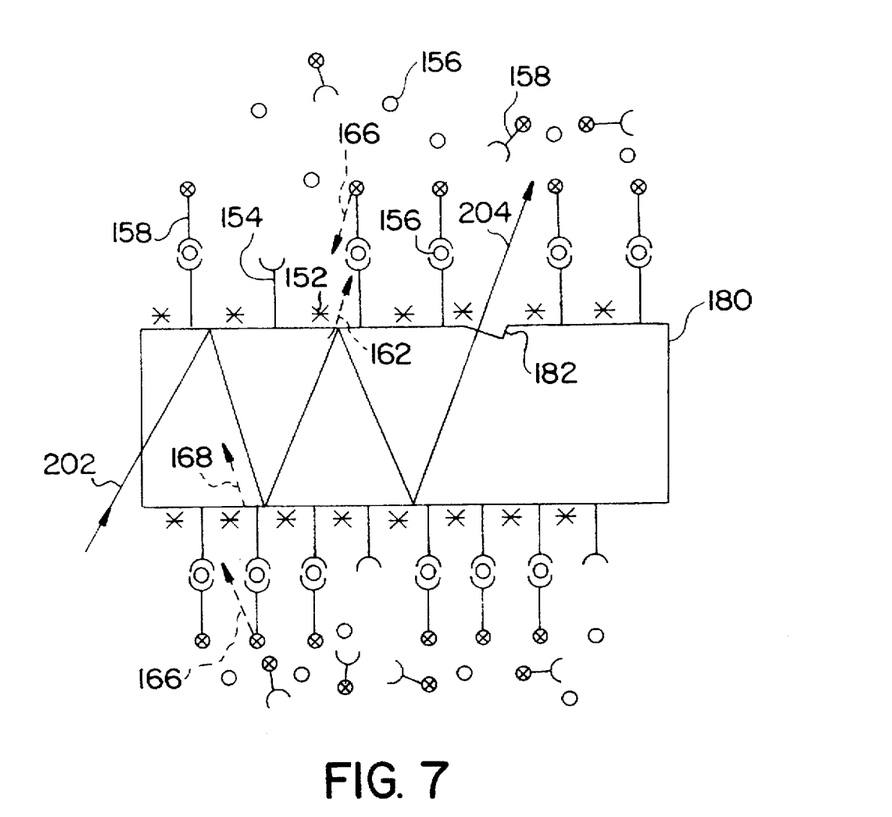
FIG. 7 is a schematic view of an evanescent wave sensor having a surface defect.

The effect of surface irregularities on a sensor is shown schematically in FIG. 7. It is noted that a sensor having a surface defect of any significance should be rejected for use in analyzing a medium for the presence of an analyte. The sensor should optimally be pretested with a reference material before contact with a test sample. In the preferred embodiment the reference material will be attached to the sensor for pretesting purposes.

In FIG. 7, a waveguide 180 contains a defect, or surface irregularity 182. Light input 202 is internally reflected along the waveguide to produce evanescent radiation however the reflection is effected by the surface irregularity 182. Such effects are undesirable because they reduce the production of evanescent waves 162 in the region distal to the defect, thereby decreasing analyte emission signal 166 and reference material emission signal 168. However, since these two signals are affected equally, their ratio will remain constant for a tested medium. Thus, the presence of the fluorophore reference material 152 acts to normalize and/or calibrate variations in signal input and signal collection.

Similarly, variation(s) in light input 202 will not affect the ratio of the analyte emission signal 166 to the reference material emission signal 168 since both will vary equally with variations in light input. Thus, in this situation, fluorophore reference material 152 acts to normalize or calibrate light input 202 thereby reducing variation(s) in light input 202.

Referring now to FIGS. 8–11, schematic representations of various embodiments of the system according to the present invention are shown. It is noted that the term optical processor as used herein shall mean any optical system that delivers excitation light to a sensor and collects the emitted light for subsequent signal processing. In the preferred embodiment, the optical processor is used for evanescent wave fluorescent measurements that measure more than one fluoromer present in the evanescent zone.

Optical processor 300, and the systems of FIGS. 8–11 include the following components:

Source (310)—Any source of electromagnetic radiation that has the spectral characteristics to cause the excitation of all of the fluoromers of interest present in the evanescent wave region.

Sensor—Sensor (312)—Any configuration of a device used for the purpose of fluorometric evanescent wave signal generation and measurement.

Coupler—Coupler (314)—An appropriate optical device for the connection of optical processor (300) to sensor (312). Coupler (314) can also be used for collection of the signal being generated by the sensor (312). Detector A—(316)—Any signal detection device optimized for Signal to Noise Ratio (SNR) for the spectrum that is transmitted by filter 3. Detector B (318).

Any signal detection device optimized for SNR for the spectrum that is transmitted by filter 2.

Element A (320)—Dual band dichroic which reflects the excitation light of the fluoromers to be measured and transmits the emission signals of the two fluoromers being measured. (It is noted that any standard beam splitter can be used but would reduce the SNR).

Element B—(322)—Dichroic that transmits the emission light of one of the fluoromers being measured and reflects the light emitted by the second fluoromer. It is noted that any standard beam splitter can be used but would reduce the SNR).

Filter 1—(324)—Dual band interference filter for transmitting the excitation light for the two fluoromers to be measured.

Filter 2—Filter 2 (326)—Interference filter that transmits the light generated by one of the fluoromers.

Filter 3 Filter (328)—Interference filter that transmits the light generated by the second fluoromer.

Figure 9:
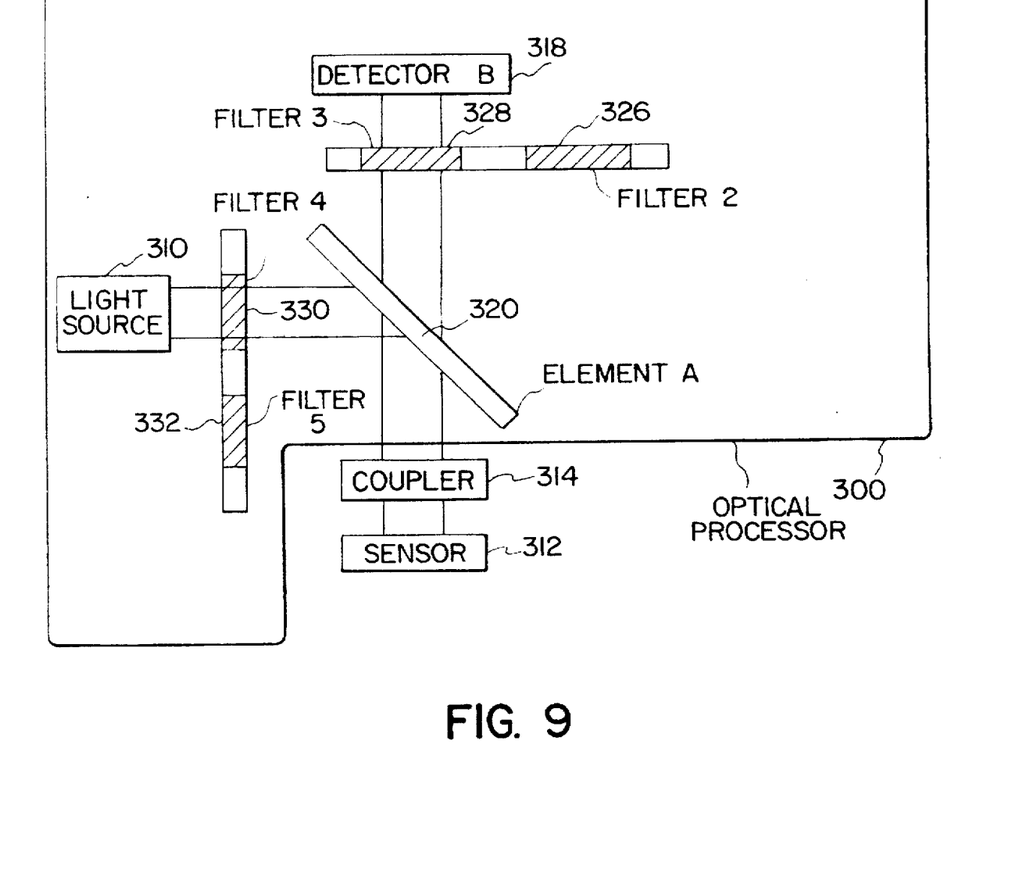
FIG. 9 is a schematic representation of another system according to the invention.
Figure 10:
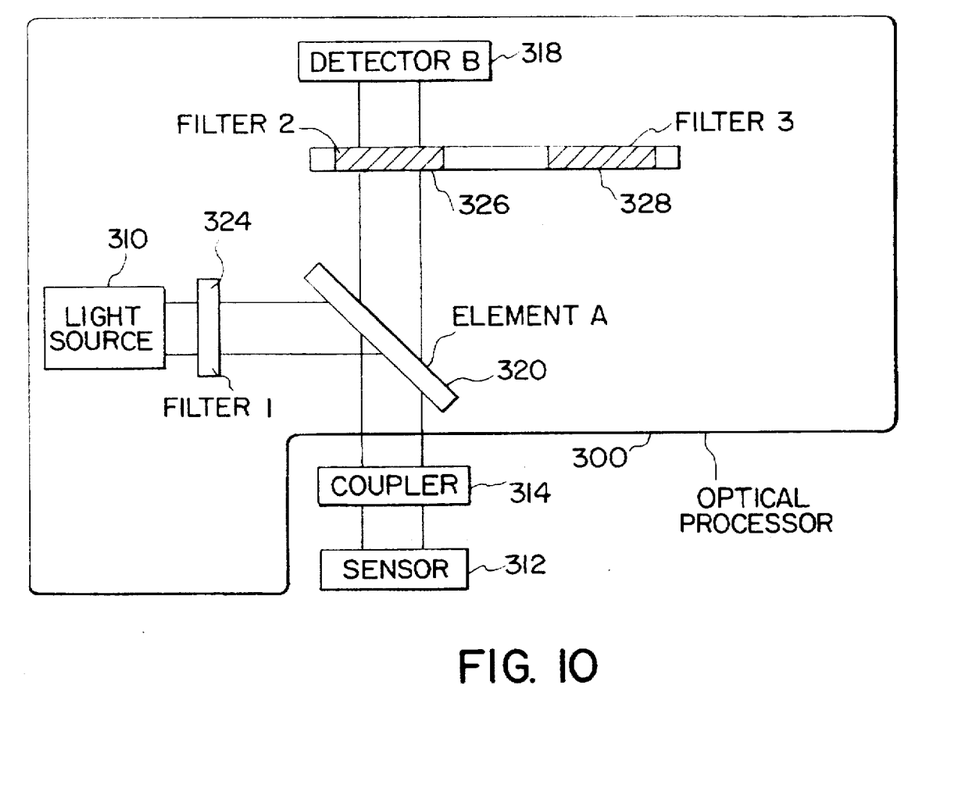
FIG. 10 is a schematic representation of another system according to the invention.
Figure 11:
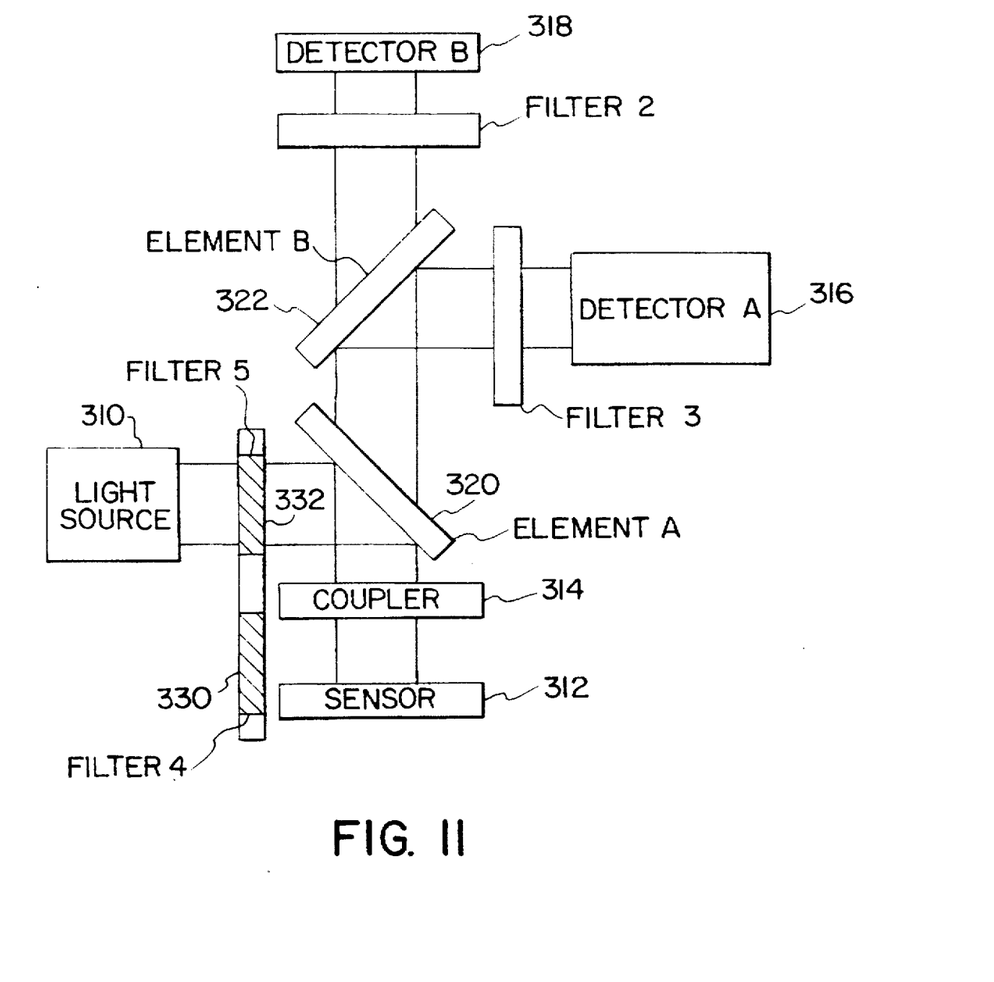
FIG. 11 is a schematic representation of another system according to the invention.

(The following elements are only used in FIGS. 9 and 11)

Filter 4—(330)—Interference filter that transmits the excitation light fort he second fluoromer being measured.

Filter 5—Filter (332)—Interference filter that transmits the excitation light for one of the fluoromers being measured.

Figure 8:
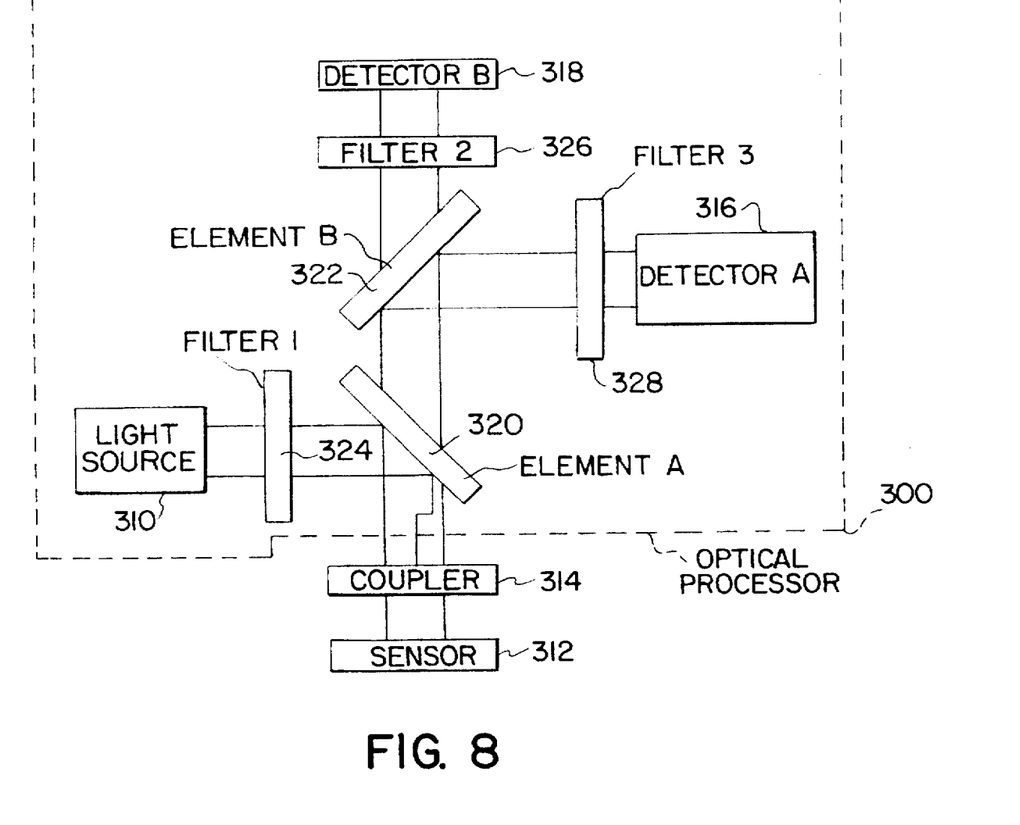
FIG. 8 is a schematic representation of a system according to the invention.

The system as shown in FIG. 8 functions as follows:

A) Filter 1 filters the light source in such a way that allows for the excitation frequencies for FITC Fluoroescein isothiocyanate and APC (Allophycocyanin) to be transmitted simultaneously in a way that these spectra can be rejected by filters 2 and 3 326 and 328. This rejection is necessary to eliminate the detector's ability to detect the excitation light. This rejection is imperative to optimize the SNR of the system.

B) Filters 2 and 3 326, 328 are optimized to transmit the emitted light of APC and FITC respectively. (See Omega Optical Technical Report "Optical Coatings for Fluorescence Instruments", August 1987, Omega Optical, Vermont; and Omega Optical Technical Report "There's No End To Light Optical Interference Filters and Coatings" 1987, Omega Optical, Vermont; both of which are incorporated herein by reference.)

C) Element A, 322 maximizes the reflection of the excitation light of APC and FITC which optimizes the system signal generation. Element A 320 at the same time maximizes the transmission of the emitted light and optimizes the signal measurement capability.

D) Element B, 322 can separate the emitted light of the APC and FITC fluorometric signals in an efficient manner by reflecting the FITC light emitted and transmitting the APC light emitted.

The invention here is unique in that it is a multifrequency multimeasurement (more than one fluoromer) system. This optical processor's capabilities differ significantly from systems known in the art.

In view of the above disclosure, alternative designs of the components of the system may be provided including: the use of a single detector to measure more than one fluoromer; the measurement of the reference signal on a surface difference from the one in which the excitation light entered the surface; the use of a system with moving i.e. moveable or interchangeable filter.

Although specific features of the invention are shown in some drawings and not in others, it is for convenience only as each feature may be combined with any or all of the other features in accordance with the invention.

It should be understood, however, that the foregoing description of the invention is intended merely to be illustrative thereof and that other modifications, embodiments and equivalents may be apparent to those skilled in the art without departing from the spirit of the invention.

What is claimed is:

1. A system for measuring at least one signal from a waveguide sensor, the system comprising:
   a waveguide sensor having at least one wave propagating surface including a reactant coating immobilized thereon, the reactant coating including a first molecular species and a labeled molecular species, the first molecular species being bound to the waveguide sensor, the first molecular species being bound to the labeled molecular species, and the labeled molecular species having an excitation wavelength and an emission wavelength;
   a fluorescent reference material attached to the waveguide, the fluorescent reference material having an excitation wavelength and an emission wavelength;
   a source capable of emitting electromagnetic radiation at the excitation wavelength of the fluorescent reference material;
   a first detector capable of detecting the emission wavelength of the fluorescent reference material; and
   a coupler for transmitting electromagnetic radiation along a first path from the source to the waveguide sensor to the first detector.

2. A system in accordance with claim 1, further comprising a first dichroic element and a first filter, the first dichroic element being disposed between the source and the waveguide sensor along the first path, the first filter being disposed between the source and the first dichroic element along the first path, the first filter being capable of transmitting electromagnetic radiation at the excitation wavelength of the labeled molecular species and the excitation wavelength of the fluorescent reference material.

3. A system in accordance with claim 2, further comprising a second dichroic element and a second filter, the second dichroic element being disposed between the waveguide sensor and the first detector along the first path, the second filter being disposed between the second dichroic element and the first detector along the first path, the second filter being capable of filtering electromagnetic radiation at the emission wavelength of the labeled molecular species.

4. A system in accordance with claim 3, further comprising a second detector capable of detecting the emission wavelength of the labeled molecular species, wherein the coupler is capable of transmitting electromagnetic radiation along a second path from the source to the waveguide sensor to the second detector, and wherein the source is capable of emitting electromagnetic radiation at the excitation wavelength of the labeled molecular species.

5. A system in accordance with claim 4, further comprising a third filter disposed between the second dichroic element and the second detector along the second path, the third filter being capable of filtering electromagnetic radiation at the emission wavelength of the fluorescent reference material.

6. A system in accordance with claim 1, further comprising a second detector capable of detecting the emission wavelength of the labeled molecular species, wherein the coupler is capable of transmitting electromagnetic radiation along a second path from the source to the waveguide sensor to the second detector, and wherein the source is capable of emitting electromagnetic radiation at the excitation wavelength of the labeled molecular species.

7. A system in accordance with claim 6, further comprising a third filter disposed between the second dichroic element and the second detector along the second path, the third filter being capable of filtering electromagnetic radiation at the emission wavelength of the fluorescent reference material.

8. A system in accordance with claim 1, wherein the labeled molecular species is selected from the group consisting of antigens, antibodies, amino acid sequences, nucleic acid sequences and mixtures thereof.

9. A system in accordance with claim 1, wherein the first molecular species is selected from the group consisting of antigens, antibodies, amino acid sequences, nucleic acid sequences and mixtures thereof.

10. A system for measuring at least one signal from an evanescent waveguide sensor, the system comprising:
    a waveguide sensor capable of emitting first and second wavelengths;
    a fluorescent reference material attached to the waveguide sensor, the fluorescent reference material having an emission wavelength approximately equal to the first wavelength;
    a source capable of emitting electromagnetic radiation at the first and second wavelengths;
    a first detector capable of detecting electromagnetic radiation at the first wavelength;
    a second detector capable of detecting electromagnetic radiation at the second wavelength; and
    a coupler for transmitting electromagnetic radiation along a first path from the source to the waveguide sensor to the first detector and along a second path from the source to the waveguide sensor to the second detector.

11. A system in accordance with claim 10, further comprising a first dichroic element and a first filter, the first dichroic element being disposed between the source and the waveguide sensor along the first and second paths, the first filter being disposed between the source and the first dichroic element along the first path, the first filter being capable of transmitting electromagnetic radiation at the first and second wavelengths.

12. A system in accordance with claim 11, further comprising a second dichroic element and a second filter, the second dichroic element being disposed between the waveguide sensor and the first detector along the first path, the second filter being disposed between the second dichroic element and the first detector along the first path, the second filter being capable of filtering electromagnetic radiation at the second wavelength.

13. A system in accordance with claim 12, further comprising a third filter disposed between the second dichroic element and the second detector along the second path, the third filter being capable of filtering electromagnetic radiation at the first wavelength.

14. A system in accordance with claim 13, further comprising a first molecular species and a labeled molecular species capable of binding to the analyte, the labeled molecular species having an emission wavelength approximately equal to the second wavelength.

15. A system in accordance with claim 14, wherein the labeled molecular species is selected from the group consisting of labeled antigens, labeled antibodies, labeled amino acid sequences, labeled nucleic acid sequences and mixtures thereof.

16. A system in accordance with claim 10, further comprising a first molecular species and a labeled molecular species, the labeled molecular species having an emission wavelength approximately equal to the second wavelength.

17. A system in accordance with claim 16, wherein the labeled molecular species is selected from the group consisting of labeled antigens, labeled antibodies, labeled amino acid sequences, labeled nucleic acid sequences and mixtures thereof.

18. A system for measuring at least one signal from a waveguide sensor, the system comprising:

a waveguide sensor having at least one wave propagating surface including a reactant coating mobilized thereon, the reactant coating including a first molecular species and a labeling molecular species, the first molecular species being bound to the waveguide sensor and the labeling molecular species having an excitation wavelength and an emission wavelength, the labeling molecular species being bound to the first molecular species;

a fluorescent reference material attached to the wave guide, the fluorescent reference material having an excitation wavelength and an emission wavelength;

a source capable of emitting electromagnetic radiation at the excitation wavelength of the fluorescent reference material;

a first detector capable of detecting the emission wavelength of the fluorescent reference material; and a coupler for transmitting electromagnetic radiation along a first path from the source to the waveguide sensor to the first detector.

19. A system in accordance with claim 18, further comprising a first dichroic element and a first filter, the first dichroic element being disposed between the source and the waveguide sensor along the first path, the first filter being disposed between the source and the first dichroic element along the first path, the first filter being capable of transmitting electromagnetic radiation at the excitation wavelength of the labeling molecular species and the excitation wavelength of the fluorescent reference material.

20. A system in accordance with claim 19, further comprising a second dichroic element and a second filter, the second dichroic element being disposed between the waveguide sensor and the first detector along the first path, the second filter being disposed between the second dichroic element and the first detector along the first path, the second filter being capable of filtering electromagnetic radiation at the emission wavelength of the labeling molecular species.

21. A system in accordance with claim 20, further comprising a second detector capable of detecting the emission wavelength of the labeling molecular species, wherein the coupler is capable of transmitting electromagnetic radiation along a second path from the source to the waveguide sensor to the second detector, and wherein the source is capable of emitting electromagnetic radiation at the excitation wavelength of the labeling molecular species.

22. A system in accordance with claim 21, further comprising a third filter disposed between the second dichroic element and the second detector along the second path, the third filter being capable of filtering electromagnetic radiation at the emission wavelength of the fluorescent reference material.

23. A system in accordance with claim 18, further comprising a second detector capable of detecting the emission wavelength of the labeling molecular species, wherein the coupler is capable of transmitting electromagnetic radiation along a second path from the source to the waveguide sensor to the second detector, and wherein the source is capable of emitting electromagnetic radiation at the excitation wavelength of the labeling molecular species.

24. A system in accordance with claim 23, further comprising a third filter disposed between the second dichroic element and the second detector along the second path, the third filter being capable of filtering electromagnetic radiation at the emission wavelength of the fluorescent reference material.

25. A system in accordance with claim 18, wherein the labeling molecular species is selected from the group consisting of labeled antigens, labeled antibodies, labeled amino acid sequences, labeled nucleic acid sequences and mixtures thereof.

26. A system in accordance with claim 18, wherein the first molecular species is selected from the group consisting of antigens, antibodies, amino acid sequences, nucleic acid sequences and mixtures thereof.

* * * * *